United States Patent
Ben-Bassat et al.

(10) Patent No.: US 6,231,607 B1
(45) Date of Patent: May 15, 2001

(54) BONE GRAFT SUBSTITUTE AND ITS PREPARATION

(75) Inventors: Hannah Ben-Bassat, Jerusalem; Sara Sarig, Karme Yosef, both of (IL)

(73) Assignees: Hadasit Medical Research Services & Development Company Ltd.; Yissum Research Development Company of the Hebrew University, both of Jerusalem (IL)

( * ) Notice: Subject to any disclaimer, the term of this patent is extended or adjusted under 35 U.S.C. 154(b) by 0 days.

(21) Appl. No.: 09/091,029

(22) PCT Filed: Dec. 19, 1996

(86) PCT No.: PCT/IL96/00182

§ 371 Date: Jun. 8, 1998

§ 102(e) Date: Jun. 8, 1998

(87) PCT Pub. No.: WO97/23428

PCT Pub. Date: Jul. 3, 1997

(30) Foreign Application Priority Data

Dec. 21, 1995 (IL) .......................................... 116477

(51) Int. Cl.$^7$ ........................................ H61F 2/28
(52) U.S. Cl. ........................................... 623/16.11
(58) Field of Search .................................... 623/16, 16.11; 501/1; 606/77; 442/59; 423/311

(56) References Cited

U.S. PATENT DOCUMENTS

| 4,861,733 | | 8/1989 | White . | |
| 5,084,051 | * | 1/1992 | Tormala et al. ........................ | 606/77 |
| 5,152,836 | | 10/1992 | Hirano et al. . | |
| 5,747,390 | * | 5/1998 | Cooper et al. ......................... | 442/59 |
| 5,885,540 | * | 3/1999 | Fulmer et al. ......................... | 423/11 |

FOREIGN PATENT DOCUMENTS

| 3925185 | | 5/1990 | (DE) . |
| 0705802 | | 4/1996 | (EP) . |
| 0705802 | * | 10/1996 | (EP) . |
| 9523775 | * | 9/1995 | (WO) . |

* cited by examiner

Primary Examiner—Michael J. Milano
Assistant Examiner—Hieu Phan
(74) Attorney, Agent, or Firm—Greer, Burns & Crain, Ltd.

(57) ABSTRACT

A solid ceramic composition comprising β-TCP, hydroxy apatite and a substantial amount of α-TCP as shown in the x-ray diffraction spectrum, which is useful as a bone graft substitute. A process for preparing the composition by subjecting a mixture of ionic calcium, phosphate, aspartic acid and carbonate to microwave irradiation and quenching the irradiated mixture.

18 Claims, 5 Drawing Sheets

BONE GRAFT SUBSTITUTE AND ITS PREPARATION

FIELD OF THE INVENTION

The present invention relates to the preparation of artificial bone or bone graft substitutes. In particular, it relates to hydroxyapatite ceramics which are suitable for this purpose.

BACKGROUND OF THE INVENTION

There are many advantages in using bone graft substitutes over transplantable allografts which include avoidance of the danger of transmitting infectious diseases to the host, they are less expensive and are more readily available. However, the mechanical strength of available substitutes is substantially lower than allografts, they lack elasticity and exhibit a poor osteoinductive capability.

During the last two decades porous, calcium and phosphate-based ceramics were developed as synthetic bone graft substitutes. Past works have shown that these substitutes are biocompatible and are easily fabricated in a variety of sizes and shapes. These ceramic compositions of matter typically comprise hydroxyapatite (hereinafter: "HA") and tricalcium phosphate (hereinafter: "TCP") or a mixture (hereinafter: "HA+TCP") thereof.

Synthetic apatites mixed with tricalcium phosphate are widely used in bones and teeth transplantation. Following preparations, the HA+TCP is usually subjected to a mechanical treatment in which the material is ground and/or pressed to obtain a required porosity, hardness or shape, partially overcoming the problems associated with the bone graft substitutes discussed above.

However, the requirement to obtain a good quality bone graft substitute still exists, as well as the need to simplify the mechanical treatment stage.

It is an object of the present invention to provide a bone substitute being suitable for use as a transplantable graft.

It is a further object of the invention to provide a process for preparing such a bone substitute.

Other objects of the invention will become apparent from the following description.

SUMMARY OF THE INVENTION

In accordance with the invention a novel process for the preparation of a composition of matter useful as a bone graft substitute has been developed. The novel process which constitutes one facet of the invention, yields a composition of matter, which is novel per se, and which constitutes another facet thereof. For reasons which are not yet fully elucidated, the novel composition of matter of the invention possesses improved properties in its use as a bone graft substitute.

The present invention provides, by a first of its aspects, a composition of matter useful as a bone graft substitute. The composition of matter of the invention comprises a mixture of tricalcium phosphate (TCP) and crystallized hydroxy apatite (HA) and is a solid mass typically formed so as to be suitable for transplantation. The composition of matter of the invention is unique in that rather than having essentially only the β form of TCP (β-TCP), it comprises both α- and β- TCP.

BRIEF DESCRIPTION OF THE DRAWINGS

FIGS. 4A and 4B are 2 days after seeding;

FIG. 4C is 14 days after seeding;

FIG. 4D is 21 days after seeding; and

DETAILED DESCRIPTION OF THE INVENTION

Figure 1:
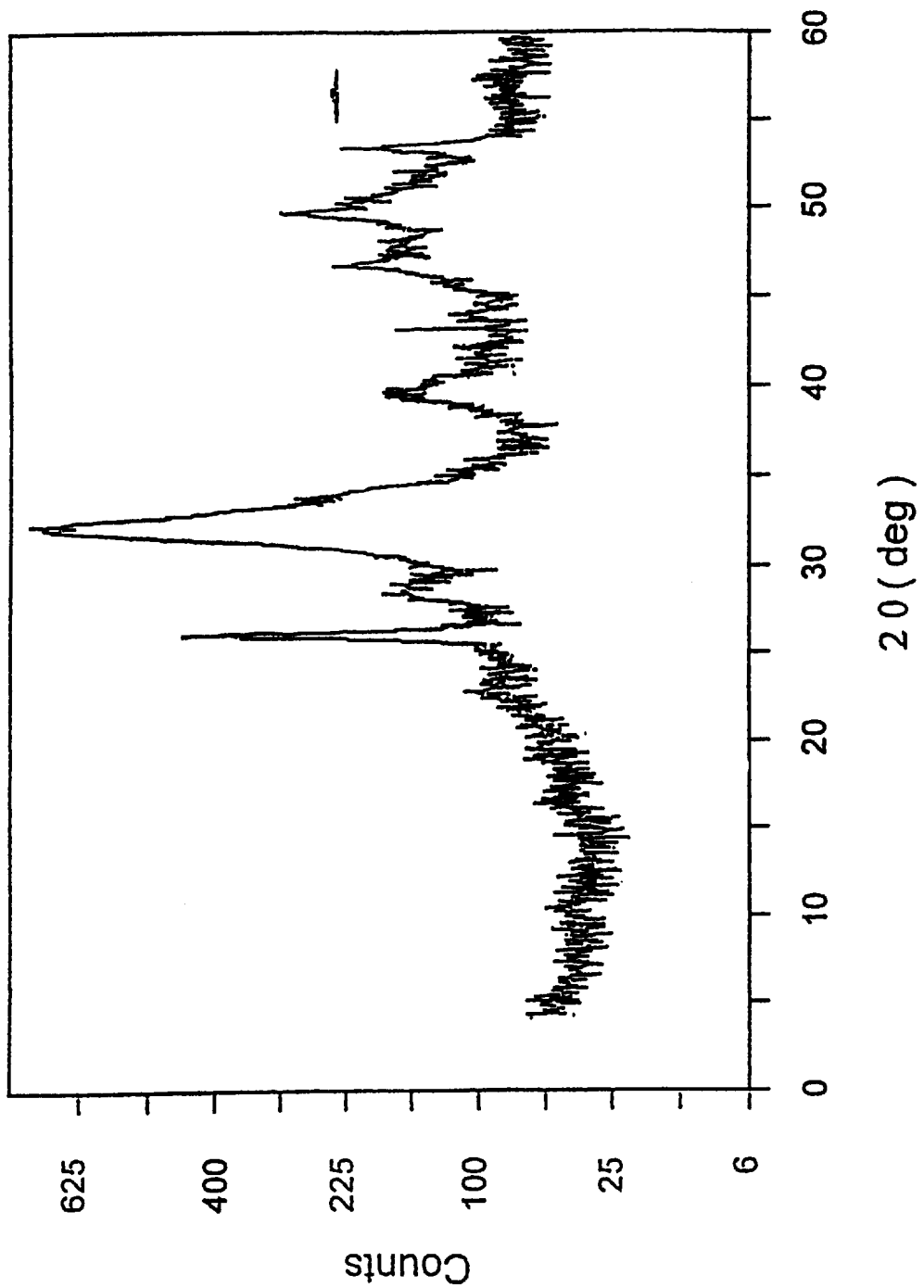
FIG. 1 is an x-ray diffraction ("XRD") spectrum showing the diffractogram of a powder product prepared in accordance with the invention prior to compression and final heating steps (after the filtering step (d) of the process)

The present invention thus provides a composition of matter, beings a solid ceramic mass and comprising β-TCP, hydroxy apatite (HA) and a substantial amount of α-TCP.

The term "substantial amount" should be understood as meaning an amount which is present in the composition of matter in noticeable quantities, i.e. not trace amounts. A substantial amount of α-TCP meaning an amount within the range of 5–40%, preferable within the range of 10–30%.

The concentration above and further below in the text will at times be given in "%". A concentration of an ingredient given in "%" means weight units of the ingredient in 100 weight units of the total composition (including that ingredient).

The presence of α-TCP in this ceramic composition of matter is evidenced, for example, in that the x-ray diffraction ("XRD") spectrum main reflection is at 2θ=30.71° and further reflections are peaked at 24.10° and 12.01°, which are characteristics of this form and do not appear in either β-TCP and HA x-ray difractograms.

In accordance with the invention a novel process for the preparation of bone graft substitute composition matter has been developed, which constitutes another aspect of the invention. This process comprises the following steps:

(a) preparing a mixture of ionic calcium, e.g. calcium chloride, phosphate, e.g. NaH$_2$PO$_4$, an amino acid in either monomeric or polymeric form, e.g., L-aspartic acid and carbonate, e.g. NaHCO$_3$;

(b) subjecting said mixture to microwave irradiation;

(c) quenching the irradiated mixture; and (d) filtering the mixture so as to separate between the filtrate and a cake and drying the cake.

According to an embodiment of the invention, the above process may further comprise the following steps:

(e) compressing the dried cake, e.g. under a pressure of 2–6 tons/cm$^2$; and (f) heating the compressed cake to a temperature of at least 650° C., e.g. to a temperature within the range of about 670–750° C., to obtain a hard ceramic mass.

Step (a) is typically carried out under controlled pH conditions, at a pH of about 7.0–8.0, preferably a pH range of about 7.3–7.5.

The microwave irradiation may typically be at a wavelength of about 2.45 GHz, at an intensity of about 700 to 1000 W, for about 5 minutes. The subsequent quenching step may be at a temperature of about 0° C. for about 30 minutes.

It should be understood that these conditions are given herein as an example only.

By a preferred embodiment of the invention, the process further comprises admixing an agent for controlling the porosity of the sintered product such as a carbonate salt, e.g. $NH_4HCO_3$, in a particulate solid form, to the cake obtained in step (d). The amount of carbonate salt added to the dried cake is typically within the range of about 5–30% by weight of the obtained mixture, preferably about 20%. Furthermore, by another preferred embodiment, the dried cake or the mixture obtained after the addition of the carbonate salt is ground prior to compression.

The powder obtained in step (d) may be used directly as bone graft, and therefore comprises another aspect of the present invention.

The $Ca^{+2}$ concentration added in step (a) is typically within the range of about $5 \times 10^{-3}$ to about $5 \times 10^{-2}$ M and the concentration of phosphate is typically within the range of about $3 \times 10^{-3}$ to about $2 \times 10^{-2}$ M; preferred $Ca^{-2}$ concentration is about $1 \times 10^{-2}$ and preferred phosphate concentration is about $6 \times 10^{-3}$M.

The aspartic acid used is preferably of the L form and its concentration in the mixture prepared in step (a) is about 10 to about 50 ppm, preferably about 25 ppm.

The carbonate concentration of in the mixture prepared in step (a) of the process of the invention is preferably about 150 to about 600 ppm. In accordance with the present invention, it was found that changing the carbonate concentration at step (a) allows to control the extent of HA to TCP conversion of the product of sep (f).

The heating in step (f) of the process is typically applied for a period of time sufficient to obtain the hardness and porosity which make the material useful as a bone substitute. The time of applied heating may also be used to advantage of controlling the final properties of the composition of matter.

EXAMPLES

Preparation Method:

Two types of solutions were prepared in a 1% Trizma buffer (pH=7.4): (A) $CaCl_2$ of $10 \times 10^{-3}$M and (B) $NaH_2PO_4$ of $6 \times 10^{-3}$M. To each one of these solutions L-Aspartic acid was added to a final concentration of 25 ppm, and $NaHCO_3$ was added to final concentrations of 150 ppm.

250 ml of each of the two types of solutions A and B, were mixed rapidly together in a 1000 ml beaker and put into a microwave (Sharp 700 w) at maximum power for 5 minutes.

The hot irradiated mixture was then quenched in an ice bath for 30 mins, and the precipitate was filtered through a milipore filter (having a pore size of 0.45 $\mu$), washed and dried at 55° C. overnight.

A limited amount of a product cake was obtained this way (about 210 mg) and this procedure was repeated several times to obtain a sufficient quantity for further analysis. The products of these batches were then collected, mixed with $NH_4HCO_3$ (20 wt %) and ground for 2 mins. (Addition of $NH_4HCO_3$ at this stage was made so as to provide the sample with a suitable porosity after being heated).

Then, portions of 200 mg each were put into a pellet dye (Graseby Specac) and compressed under pressure of 4 tons/$cm^2$. The so formed pellets were then heated to 700° C. in a standard oven for one hour. Thereafter, the samples were all analyzed by XRD and FTIR methods.

Analyses

X-ray analyses were carried out by using a Philips X-ray powder diffractometer of monochromatic Cu $K\alpha$ radiation.

FTIR analyses were performed using a Nicolet 510 FTIR spectrophotometer.

The amount of carbonate in the samples was estimated from the FTIR spectra according to a method described in[1] which is hereby incorporated by reference.

CHEMICAL RESULTS

The material HA-SAL2 according to the present application has been used both as a powder and as a sintered porous ceramic. The two products differ from each other with respect to crystallinity of the hydroxy-apatite phase, which may be seen from the undifferentiated peak of 2θ in the 32°–33° range of the powder as shown in FIG. 1, and the differentiated peaks of the sintered product in the same region, presented in FIG. 3. The x-ray diffractogram of the powder resembles closely the diffractogram of bone mineral.

Another noticeable difference between both products is their crystallography. During the sintering process, part of the initial HA powder undergoes transformation to TCP. The transformation to β-TCP was expected, in accordance with the prior art, however, under the process conditions described above, the appearance of α-TCP was not expected.

Figure 3:
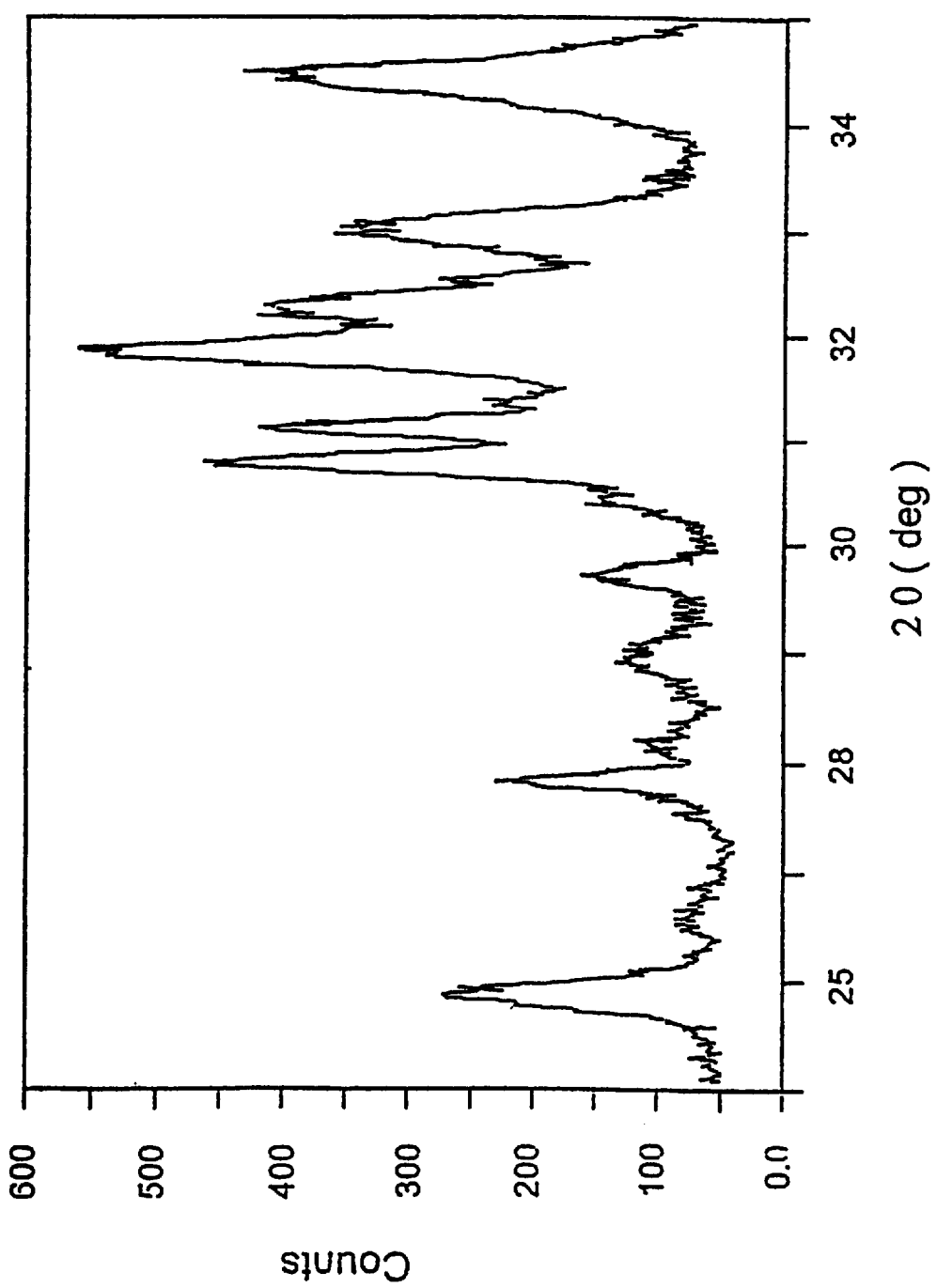
FIG. 3 is an XRD spectrum of a pellet made by two minutes grinding of the product shown in FIGS. 1 and 2, pressing under 4 tons/cm$^2$ and sintered at 700° C. (this product is referred to herein as "HA-SAL2")

Within the interval 2θ=30°–33°, the following peaks as presented in FIG. 3 were found: (i) 31.77°, 32.20°, and 32.90° of the main diffractions hydroxyapatite (JCPDS-ICDD 9-432), (ii) 31.03°, the main diffraction of β-TCP (JCPDS-ICDD 9-169) and (iii) at 30.71° the main diffraction of (α-TCP (JCPDS-ICDD 29-359). The identification of the last mentioned polymorph, was corroborated by the distinguishing(, reflections of 2θ=12.01° and 24.10° in an extended diffractogram of the same pellets (not shown).

The ratio between α- and β- TCP polymorphs depend upon various parameters, some of which are chemical, whereas the others are a function of the operating conditions. Thus, under standard operating conditions the balance between both polymorphs may depend upon the amount of $NaHCO_3$ added to the reaction mixture in step (a). The balance further depends upon the operating parameters such as the pressure applied prior to sintering, the grinding of the powder (grinding intensity and duration), temperature and sintering period.

Upon heating the powder to 700° C., the carbonate and $H_2O$ peaks of the ceramic materials at 1400 to 1600 $cm^{-1}$ are considerably weakened, whereas the 1035 $cm^{-1}$ and 565 to 633 $cm^{-1}$ peaks of phosphate compounds remain unchanged.

The transition from the powder to the porous sintered ceramic involves the addition of $NH_4HCO_3$. This substance is completely decomposed upon heating to 700° C., leaving large pores in the product's structure.

The use of the composition of the present invention in biological tests and in animal model can be made with both products, namely, the powder and the sintered ceramic. The selection of the particular state of the material is determined in accordance with the specific application.

Figure 2:
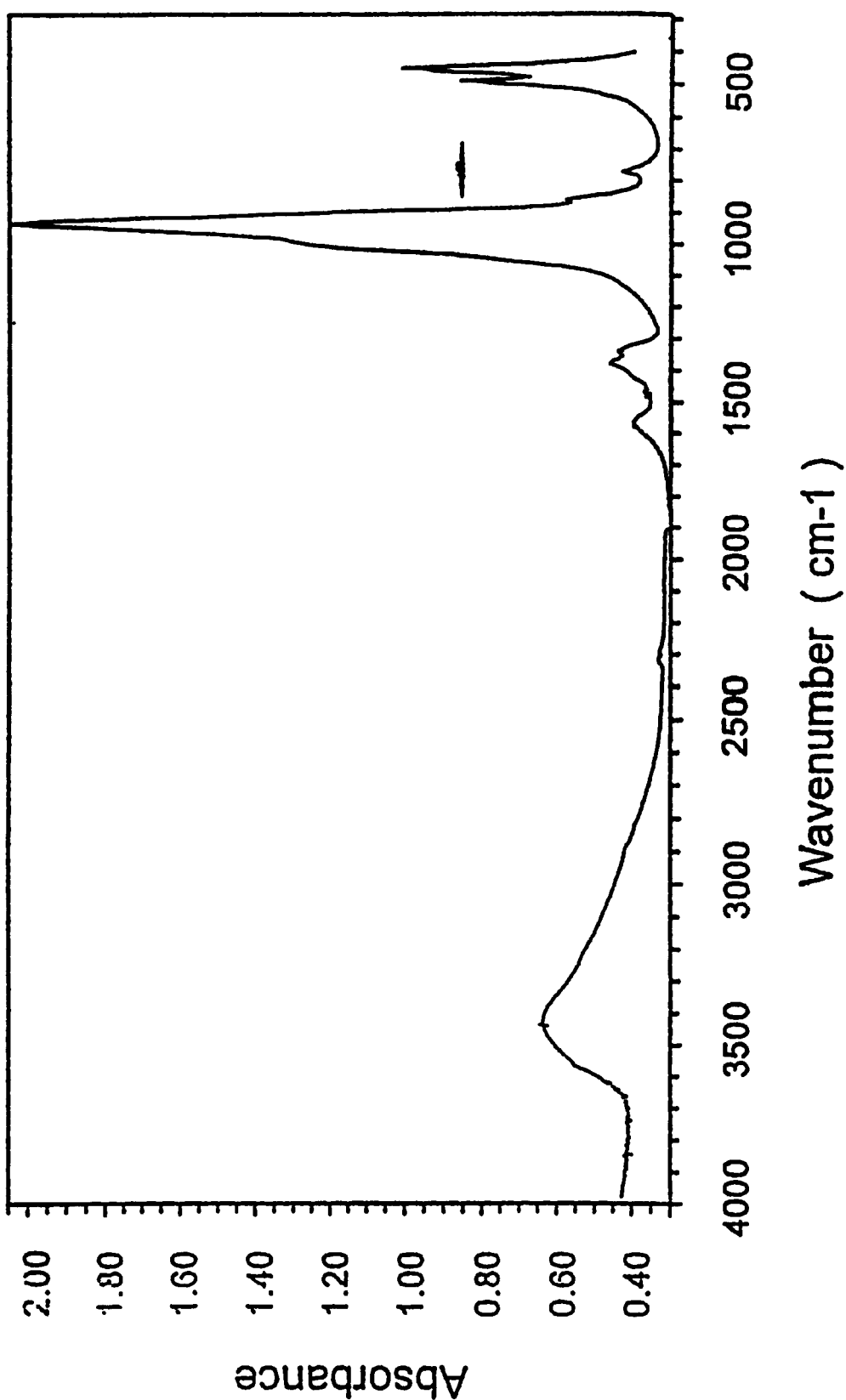
FIG. 2 is the Fourier Transform Infra Red ("FTIR") spectrum of the same product shown in FIG. 1.

In the following examples ceramic discs produced from HA-SAL2 powder were used in the biocompatibility tests, whereas the powder form was used in the animal model studies. The characterization of the initial powder used is given by its XRD spectrum (FIG. 1) and FTIR spectrum (FIG. 2).

Morphological Appearance and Growth of Human Bone Cells on HA-SAL2

Figure 4:
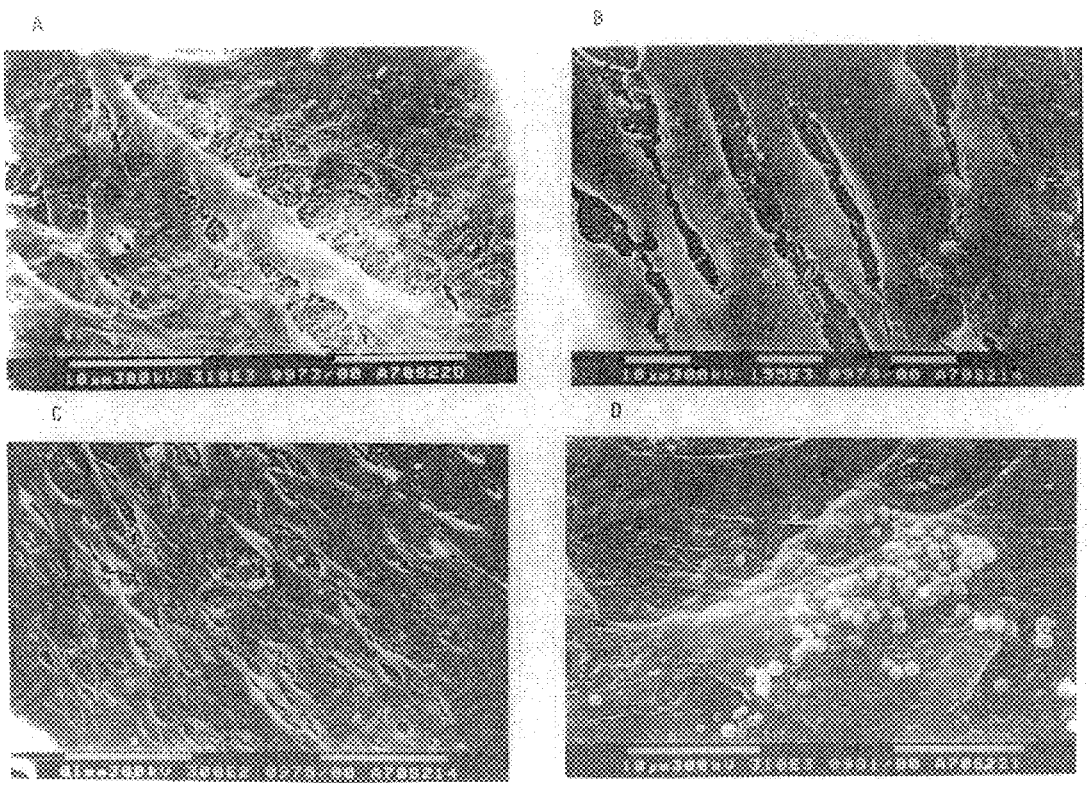
FIG. 4 are SEM ("scanning electron microscope") photographs of human osteocytes seeded on ceramic HA-SAL2.

Human bone derived cells were seeded on discs of HA-SAL2 specified under "Chemical Results", and examined by SEM after 2, 14 and 21 days of culture. Ultrastructural observation indicated that the cells had anchored, attached and spread onto the discs within 2 days after seeding (FIG. 4A). The cells were well spread, displaying a flat configuration and good contact with neighboring cells (FIG. 4B). Within 14 days after seeding, the cells had colonized large areas of the substrate surface (FIG. 4C). They maintained physical contact with one another through multiple extensions, and formed a multilayer sheet. They overlapped and superimposed, making it difficult to distinguish the borders of individual cells. Cells seeded at higher density took less time to cover the apatite surface, although there were variations from one culture batch to another. No signs of cytotoxicity or cell degenerations were evident throughout the experiment. The cells retained their typical broad and flattened morphology and exhibited good culture organization.

Concurrent with continuous cultivation of the human bone derived cells, formation of extracellular matrix ("ECM") containing fibrous material secreted by the osteoblasts could be observed (FIG. 4B). It has not been yet identified or distinguished as collagen. Globular masses on the cell surface of bone cells in culture were also observed (FIG. 4D). It has been suggested that the mineralization begins with matrix vesicles and is followed by additional mineral deposition on collagen fibrils.

The ceramic surfaces of HA-SAL2 did not exhibit microscopic degradation or altered surface morphology resulting from their interaction with the cultured cells and/or incubation in protein containing medium for the duration of the experiments.

Light microscopic and SEM examination of the periphery of the specimens and the outgrowth of the cells on the culture dishes showed no signs of toxicity throughout the rest period. The cells were well spread, maintained contact with neighboring cells, and formed a well organized monolayer. Mineralized bone-like nodules were detected by Alizarine red staining in the culture growing at the periphery of the apatite disc (generally detectable after 10 days of culturing).

Mineralization of HA-SAL2 Implanted in Rat Tibiae

According to sporadic clinical reports, HA ceramics have been used for filling bone defects in tibial plateau fractions and in bone tumor surgery. However, it was difficult to follow healing progression in these patients. In [3], the use of DEXA in vivo for detecting small changes of mineral content (MC) within a ceramic implant in a surgical model was demonstrated. This publication is incorporated herein by reference. In accordance with the model, HA cylinders were implanted in rat proximal tibiae and followed for 13 weeks. In order to determine whether the MC changes obtained in vivo by the DEXA technique are comparable with changes determined by invasive techniques commonly used to evaluate bone healing, the alkaline phosphatase (ALP) activity within the implants was measured during callus formation. The increase in ALP activity within the implants was found to precede the increase in mineral content as measured non-invasively by the DEXA technique. This was consistent with the timing of ALP activity in respect to mineralization as it occurs during fracture healing. HA-SAL1 (a preliminary preparation of the HA-SAL series) cylindrical implants of 3 mm diameter and 5 mm length were shaped and autoclaved. The results showed that DEXA imaging is useful in measuring bone ingrowth in small ceramic HA implants in vivo, despite the high mineral content background of the implant scaffold[3].

The previously described surgical model was used with some modifications[3]. In a new set of experiments, Sabra female rats weighing 250 gr were anesthetized and holes of 3 mm diameter were drilled in the right tibial metaphysis, 3 mm below the collateral ligaments insertion. HA-SAL2 powder was put in these holes, the contralateral empty holes, as control defects, were omitted since they were found to be inappropriate controls.

Figure 5:
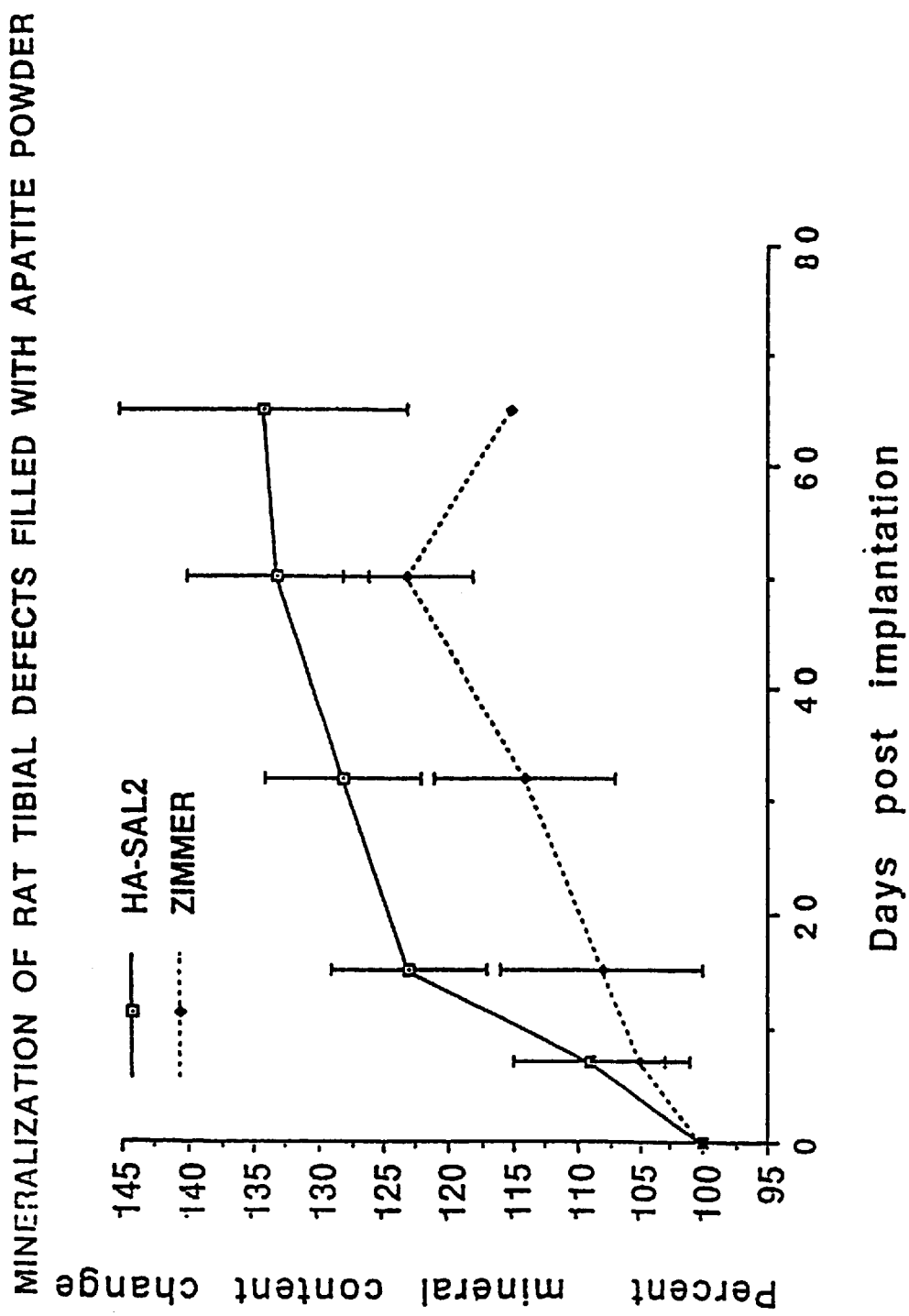
FIG. 5 is a comparison of the mineral content at a site of induced bone defects implanted with either HA-SAL2 or the commercial product Zimmer HA of Zimmer Inc., Warsaw, USA.

Bone defects implanted with HA-SAL2 powder were examined for MC at different time intervals during, 110 post implantation (days and compared to Zimmer HA (FIG. 5). The base line MC for each implanted defect was determined on Day 1 post implantation and designated "100%". MC was measured seven times post implantation (throughout the experiment). The MC change (MCC) for each implant consists of the ratio between the measured MC at each time interval and its own Day 1 MC value. In FIG. 2 the mean MCC±SEM is expressed in percent deviation from the 100% base line MC. On day 110 a maximum mean increase exceeding 50% in the MC of the HA-SAL2 implants, was observed. This resulted from apposition of healing fractured-bone callus on the surface of the powder HA-SAL2 which showed progressive mineralization. Lower MCC was obtained while using implants prepared from the product of Zimmer company, which served as controls. The substantial mineralization onto the HA-SAL2 surface, despite the lack of macropores, is indicative of its biocompatibility in vivo.

REFERENCES

1. Featherstone, J. D. B. et al., *Caries Res.*, 18:65, (1975).

2. Conistantz, B. R. et al., *Science*, 267:1796–1799, (1995).

3. Mosheiff, R., et al., *Biomaterials*, 13:(7)462–466, (1992).

What is claimed is:

1. A composition of matter, being a solid ceramic mass and comprising β-TCP, hydroxy apatite and a substantial amount of α-TCP.

2. A composition according to claim 1, wherein the concentration of α-TCP is within the range of 5–40% (w/w).

3. A process for the preparation of a composition of matter useful as a bone substitute, comprising the steps of:
   (a) preparing a mixture of ionic calcium, phosphate, aspartic acid and carbonate;
   (b) subjecting the mixture to microwave irradiation;
   (c) quenching the irradiated mixture; and
   (d) filtering the mixture so as to separate between the filtrate and a cake and drying the cake.

4. A process according to claim 3, further comprising:
   (e) compressing the dried cake; and
   (f) heating the compressed cake to a temperature of at least 650° C.

5. A process according to claim 3, wherein the mixture prepared in step (a) comprises calcium chloride, sodium phosphate, L-Aspartic acid and sodium carbonate.

6. A process according to claim 3 comprising admixing a carbonate salt in particulate solid form to the cake obtained in step (d).

7. A process according to claim 3, comprising grinding the cake obtained in step (d).

8. A process according to claim 4, wherein the step of heating the compressed cake further comprises maintaining a temperature essentially constant for a period of time.

9. A composition of matter obtained by the process of claim 3.

10. The composition of matter of claim 1, wherein said composition of matter is a bone graft substitute.

11. A composition of matter obtained by the process of claim 4.

12. A composition of matter obtained by the process of claim 5.

13. A composition of matter obtained by the process of claim 6.

14. A composition of matter obtained by the process of claim 7.

15. A composition of matter obtained by a process of claim 8.

16. The composition of matter of claim 2, wherein the composition of matter is a bone graft substitute.

17. The composition of matter of claim 9, wherein the composition of matter is a bone graft substitute.

18. The composition of matter of claim 1, wherein said composition of matter is a ceramic formed by heating to no more than approximately 750° C.

* * * * *